| (12) | United States Patent | (10) Patent No.: | US 12,102,322 B2 |
|---|---|---|---|
| | Baril et al. | (45) Date of Patent: | Oct. 1, 2024 |

(54) BUTTRESS ATTACHMENT FOR SURGICAL STAPLING APPARATUS

(71) Applicant: Covidien LP, Mansfield, MA (US)

(72) Inventors: Jacob C. Baril, Norwalk, CT (US); Roanit Fernandes, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/206,266

(22) Filed: Jun. 6, 2023

(65) Prior Publication Data

US 2023/0309995 A1 Oct. 5, 2023

Related U.S. Application Data

(62) Division of application No. 17/365,059, filed on Jul. 1, 2021, now Pat. No. 11,678,879.

(51) Int. Cl.
*A61B 17/072* (2006.01)
*A61B 17/068* (2006.01)

(52) U.S. Cl.
CPC ........ *A61B 17/0686* (2013.01); *A61B 17/072* (2013.01); *A61B 17/07292* (2013.01);
(Continued)

(58) Field of Classification Search
CPC . A61B 17/068; A61B 17/0686; A61B 17/072; A61B 17/07207; A61B 17/07292;
(Continued)

(56) References Cited

U.S. PATENT DOCUMENTS

| 3,054,406 A | 9/1962 | Usher |
|---|---|---|
| 3,124,136 A | 3/1964 | Usher |
| | (Continued) | |

FOREIGN PATENT DOCUMENTS

| CA | 2282761 A1 | 9/1998 |
|---|---|---|
| DE | 1602563 U | 3/1950 |
| | (Continued) | |

OTHER PUBLICATIONS

Extended European Search Report corresponding to EP 14 16 9739.1, completed Aug. 19, 2014 and dated Aug. 29, 2014; (7 pp).

(Continued)

*Primary Examiner* — Scott A Smith

(57) ABSTRACT

A surgical stapling apparatus includes a loading unit and a surgical buttress assembly. The loading unit includes an anvil assembly and a staple cartridge assembly. The staple cartridge assembly includes a staple cartridge having a tissue facing surface including staple pockets and a central longitudinal slot defined therethrough and a hook assembly extending outwardly from the tissue facing surface. The surgical buttress assembly includes an anvil buttress and a cartridge buttress. Each of the anvil and cartridge buttresses includes a body, a proximal tab, and a distal tab. The anvil and cartridge buttresses are interconnected at a junction of the proximal tabs and the surgical buttress assembly is folded at the junction such that the proximal tabs substantially overlie one another. The proximal tabs are engaged with the hook assembly to releasably secure the proximal tabs of the anvil and cartridge buttresses to the staple cartridge assembly.

20 Claims, 12 Drawing Sheets

(52) U.S. Cl.
CPC ....... *A61B 17/068* (2013.01); *A61B 17/07207* (2013.01); *A61B 2017/07214* (2013.01); *A61B 2017/07264* (2013.01); *A61B 2017/07271* (2013.01)

(58) Field of Classification Search
CPC ........ A61B 17/115; A61B 2017/00477; A61B 2017/07214; A61B 2017/07228; A61B 2017/07271
USPC ..... 227/19, 175.1, 176.1, 180.1; 606/1, 139, 606/219
See application file for complete search history.

(56) References Cited

U.S. PATENT DOCUMENTS

| | | |
|---|---|---|
| 3,364,200 A | 1/1968 | Ashton et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |

(56) References Cited

U.S. PATENT DOCUMENTS

| | | |
|---|---|---|
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |

(56) References Cited

U.S. PATENT DOCUMENTS

| | | |
|---|---|---|
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 11,065,000 B2 | 7/2021 | Shankarsetty et al. |
| 11,337,699 B2* | 5/2022 | Taylor .............. A61B 17/07292 |
| 11,399,833 B2* | 8/2022 | Abramek .......... A61B 17/07292 |
| 11,419,608 B2* | 8/2022 | (Prommersberger) Stopek .......... A61B 17/07207 |
| 11,426,163 B2* | 8/2022 | Williams ............ A61B 17/1155 |
| 11,432,818 B2* | 9/2022 | Williams ............ A61B 17/115 |
| 11,510,670 B1* | 11/2022 | Baril ..................... A61B 17/072 |
| 11,678,879 B2 | 6/2023 | Baril et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |

(56) References Cited

U.S. PATENT DOCUMENTS

| | | |
|---|---|---|
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | De La Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0080336 A1 | 4/2012 | Shelton, IV et al. |
| 2012/0116416 A1 | 5/2012 | Neff et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153636 A1 | 6/2013 | Shelton, IV et al. |
| 2013/0153641 A1 | 6/2013 | Shelton, IV et al. |
| 2013/0256380 A1 | 10/2013 | Schmid et al. |
| 2014/0034704 A1 | 2/2014 | Ingmanson et al. |
| 2014/0048580 A1 | 2/2014 | Merchant et al. |
| 2014/0131418 A1 | 5/2014 | Kostrzewski |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157321 A1 | 6/2015 | Zergiebel et al. |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310134 A1 | 10/2016 | Contini et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | Stopek et al. |
| 2019/0021734 A1 | 1/2019 | Hodgkinson |
| 2019/0059878 A1 | 2/2019 | Racenet et al. |
| 2019/0083087 A1 | 3/2019 | Viola et al. |
| 2019/0254671 A1 | 8/2019 | Shankarsetty |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2491867 A1 | 8/2012 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 9516221 A1 | 6/1995 |
| WO | 9838923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

OTHER PUBLICATIONS

Extended European Search Report corresponding to EP 14 15 7997.9, completed Sep. 9, 2014 and dated Sep. 17, 2014; (8 pp).

Extended European Search Report corresponding to EP 14 16 8904.2, completed Sep. 10, 2014 and dated Sep. 18, 2014; (8 pp).

Extended European Search Report corresponding to EP 13 19 4995.0, completed Jun. 5, 2014 and dated Oct. 13, 2014; (10 pp).

Extended European Search Report corresponding to EP 13 15 4571.7, completed Oct. 10, 2014 and dated Oct. 2014; (8 pp).

Extended European Search Report corresponding to EP 14 18 1125.7, completed Oct. 16, 2014 and dated Oct. 24, 2014; (7 pp).

Extended European Search Report corresponding to EP 14 18 1127.3, completed Oct. 16, 2014 and dated Nov. 10, 2014; (8 pp).

Extended European Search Report corresponding to EP 14 19 0419.3, completed Mar. 24, 2015 and dated Mar. 30, 2015; (6 pp).

European Office Action corresponding to EP 12 198 776.2 dated Apr. 7, 2015.

European Office Action corresponding to EP 13 156 297.7 dated Apr. 10, 2015.

Australian Examination Report No. 1 corresponding to AU 2011250822 dated May 18, 2015.

(56) References Cited

OTHER PUBLICATIONS

European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
European Search Report corresponding to EP 06 00 4598, completed Jun. 22, 2006; (2 pp).
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.

(56) References Cited

OTHER PUBLICATIONS

Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
Australian Examination Report No. 1 corresponding to AU 2014200793 dated Sep. 2, 2017.
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
International Search Report and Written Opinion issued in corresponding International Application No. PCT/IB2022/056052 dated Nov. 29, 2022, 16 pages.
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).

(56) References Cited

OTHER PUBLICATIONS

Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 182911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
European Office Action corresponding to EP 14 17 2681.0 dated May 13, 2016.

\* cited by examiner

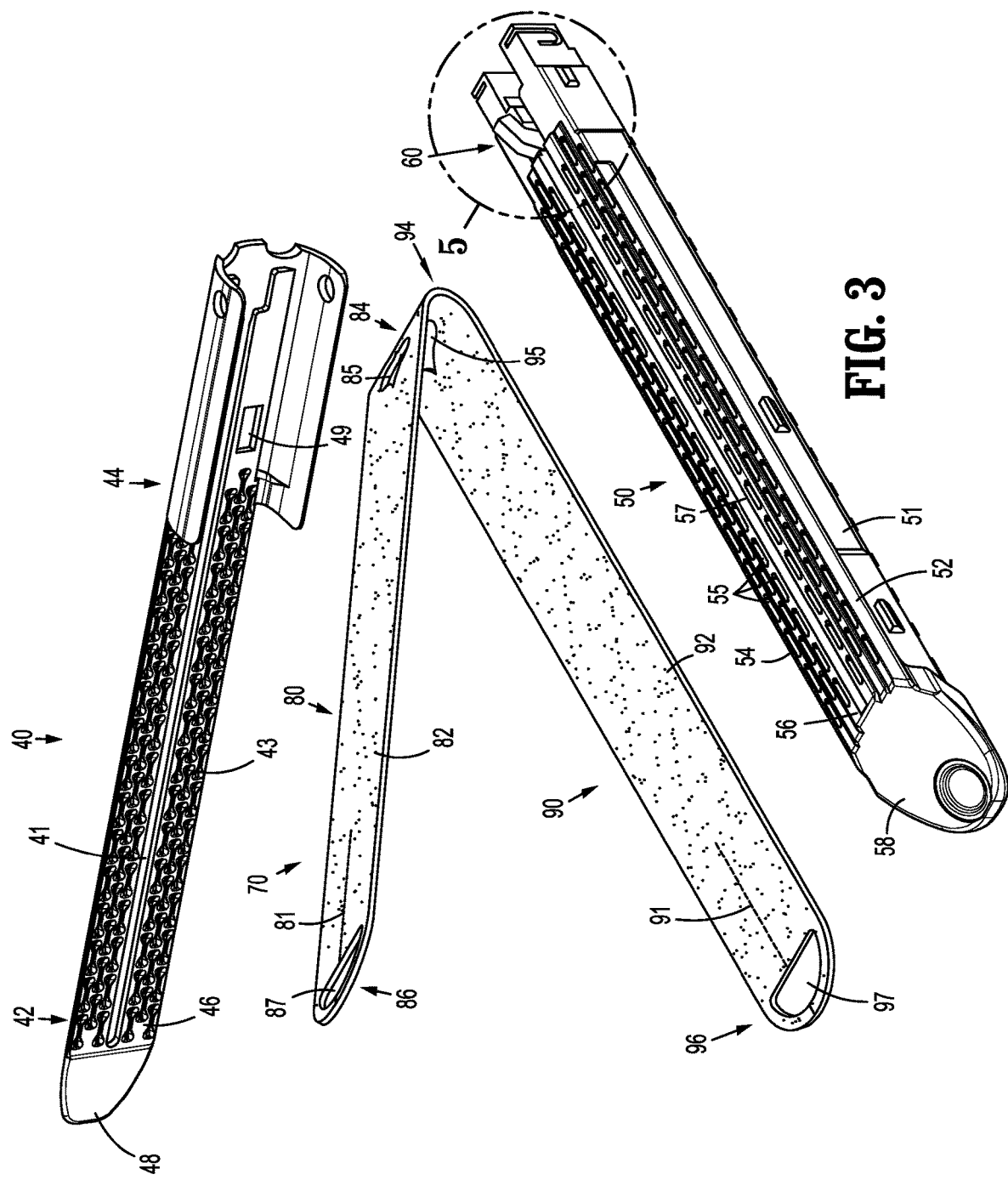

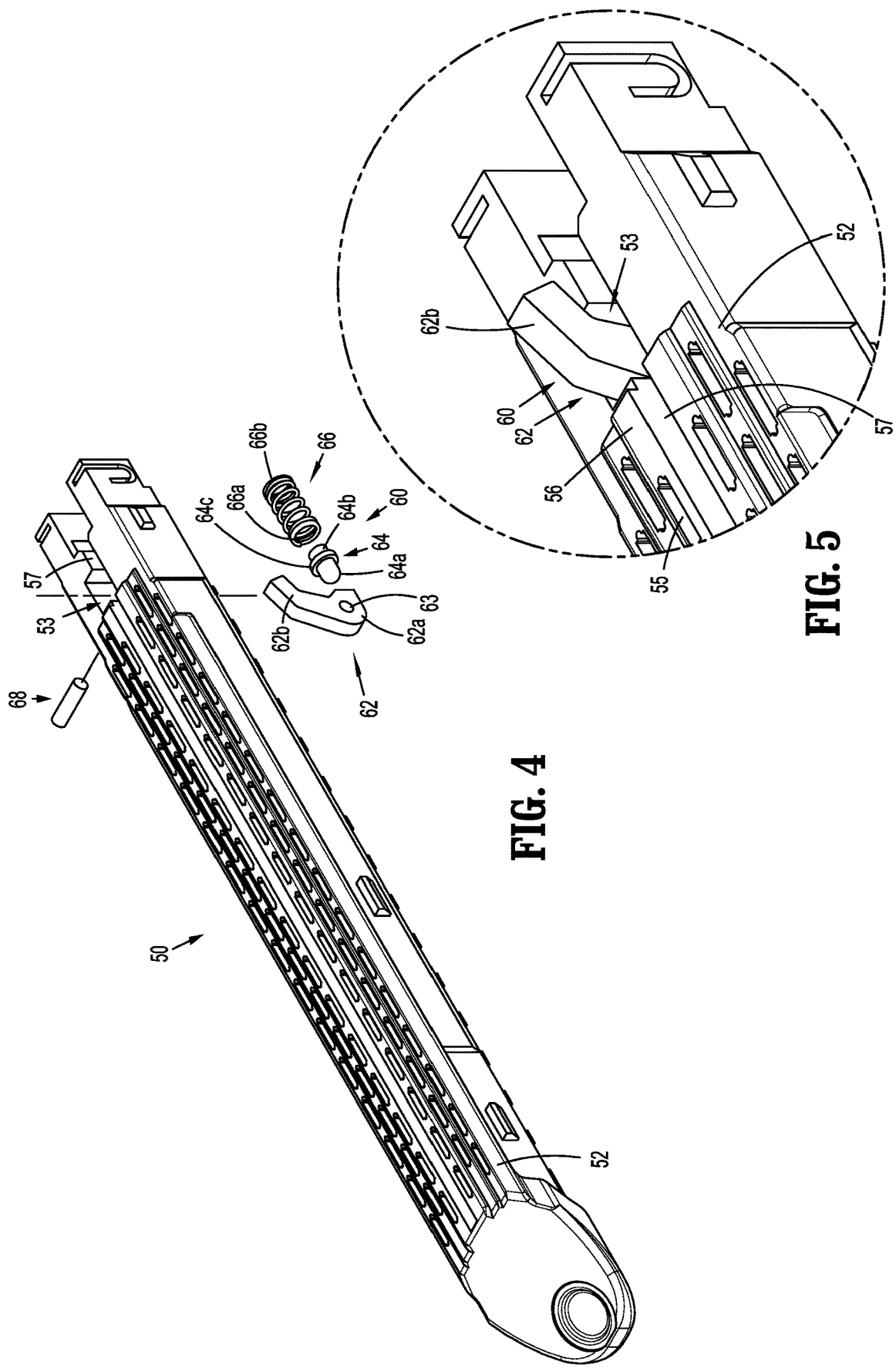

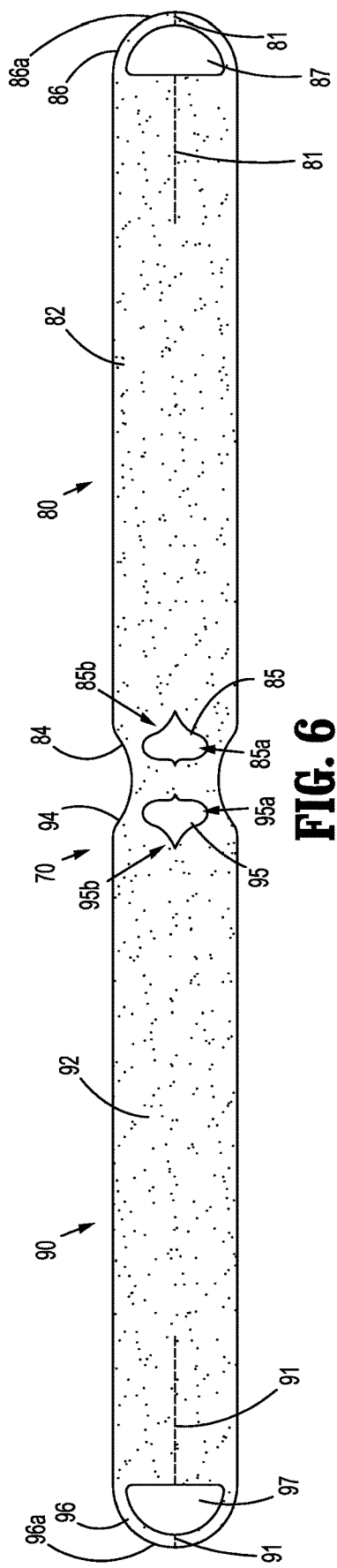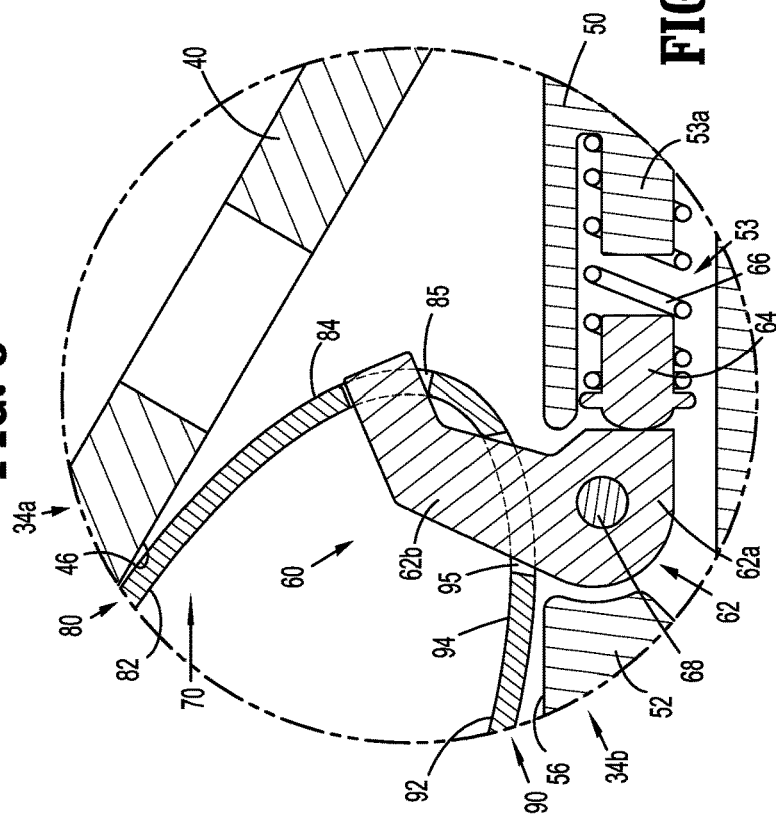

BUTTRESS ATTACHMENT FOR SURGICAL STAPLING APPARATUS

CROSS-REFERENCE TO RELATED APPLICATIONS

This application is a divisional of U.S. patent application Ser. No. 17/365,059 (now U.S. Pat. No. 11,678,879), filed Jul. 1, 2021, the entire content of which is hereby incorporated by reference herein.

FIELD

The present application is generally related to surgical stapling apparatus, and more particularly, to surgical buttresses and buttress attachment assemblies for releasably securing the surgical buttresses to the surgical stapling apparatus.

BACKGROUND

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in the jaws of the apparatus to cut the body tissue between the lines of staples.

Surgical supports, e.g., meshes or buttress materials, may be used in combination with surgical stapling apparatus to bridge, repair, and/or reinforce tissue defects within a patient. A clinician may manually attach the buttress materials to the surgical stapling apparatus in the operating room during a surgical procedure, or utilize a surgical stapling apparatus including buttress materials pre-installed thereon, e.g., by an expensive automated attachment process. The buttress material reinforces the staple or suture line as well as covers the juncture of the body tissues to reduce leakage prior to healing.

SUMMARY

The present disclosure relates to buttress material attachment onto a surgical stapling apparatus. Surgical buttresses and buttress attachment assemblies of this disclosure are designed to make buttress material attachment in the operating room a simple, straightforward, and cost-effective procedure.

In one aspect, the present disclosure provides a surgical stapling apparatus including a loading unit and a surgical buttress assembly. The loading unit includes an anvil assembly and a staple cartridge assembly. The staple cartridge assembly includes a staple cartridge having a tissue facing surface including staple pockets and a central longitudinal slot defined therethrough and a hook assembly extending outwardly from the tissue facing surface. The surgical buttress assembly includes an anvil buttress and a cartridge buttress. Each of the anvil and cartridge buttresses includes a body, a proximal tab, and a distal tab. The anvil and cartridge buttresses are interconnected at a junction of the proximal tabs and the surgical buttress assembly is folded at the junction such that the proximal tabs substantially overlie one another. The proximal tabs are engaged with the hook assembly of the staple cartridge to releasably secure the proximal tabs of the anvil and cartridge buttresses to the staple cartridge assembly.

The hook assembly may be disposed proximal to the staple pockets defined in the tissue facing surface of the staple cartridge. The proximal tabs of the anvil and cartridge buttresses may define proximal openings therethrough and the hook assembly may extend through the proximal openings. The proximal openings may extend across the central longitudinal slot defined in the staple cartridge.

The hook assembly may include a hook having a hook body disposed within a cavity defined in the staple cartridge and a finger extending proximally from the hook body and out of the cavity. The cavity of the staple cartridge may be disposed adjacent to the central longitudinal slot. The hook assembly may include a coupler and a spring disposed within the cavity of the staple cartridge, and the spring may bias the coupler into contact with the hook body. The anvil assembly may include a window defined therethrough that is aligned with the finger of the hook assembly and wherein, when the loading unit is in a closed position, the finger may extend into the window of the anvil assembly.

The distal tabs of the anvil and cartridge buttresses may define distal openings therethrough. An anvil tip of the anvil assembly may extend through the distal tab of the anvil buttress and a cartridge tip of the staple cartridge assembly may extend through the distal tab of the cartridge buttress to releasably secure the distal tabs of the anvil and cartridge buttresses to the anvil and staple cartridge assemblies. The distal tabs may include perforations defined therein. The perforations may be aligned with the central longitudinal slot of the staple cartridge.

In another aspect, this disclosure provides a surgical stapling apparatus including a loading unit and a cartridge buttress. The loading unit includes an anvil assembly and a staple cartridge assembly. The staple cartridge assembly includes a staple cartridge having a cartridge body and a cartridge tip extending distally from the cartridge body. The cartridge body includes a tissue facing surface having staple pockets and a central longitudinal slot defined therethrough and a hook assembly extending outwardly from the tissue facing surface. The cartridge buttress includes a body, a proximal tab extending proximally from the body, an expandable region extending distally from the body, and a distal tab extending distally from the expandable region. The proximal tab is engaged with the hook assembly of the staple cartridge for releasably securing the proximal tab of the cartridge buttress to the staple cartridge assembly and the distal tab is engaged with the cartridge tip for releasably securing the distal tab of the cartridge buttress to the staple cartridge assembly.

The expandable region of the cartridge buttress may be transitionable between an unexpanded state and an expanded state to elongate the cartridge buttress during loading onto the staple cartridge assembly. The expandable region may be formed from an elastic material. The body and the proximal and distal tabs of the cartridge buttress may be formed from a relatively rigid material as compared to the elastic material of the expandable region. The expandable region may include a pair of bands interconnecting the body and the distal tab.

The proximal tab of the cartridge buttress may define a proximal opening therethrough and the hook assembly may extend through the proximal opening. The proximal opening of the proximal tab may extend across the central longitudinal slot defined in the staple cartridge. The distal tab of the cartridge buttress may define a distal opening therethrough and the cartridge tip may extend through the distal opening.

The hook assembly may include hooks disposed on opposed sides of the central longitudinal slot of the staple cartridge. Each of the hooks may include an arm secured to the tissue facing surface of the staple cartridge and a finger extending proximally from the arm.

The details of one or more aspects of this disclosure are set forth in the accompanying drawings and the description below. Other aspects, as well as features, objects, and advantages of the aspects described in this disclosure will be apparent from the description and drawings, and from the claims.

BRIEF DESCRIPTION OF DRAWINGS

Various aspects of the present disclosure are described hereinbelow with reference to the drawings, which are incorporated in and constitute a part of this specification, wherein:

FIG. 3 is a perspective view, with parts separated, of the tool assembly of FIG. 2, showing an anvil assembly, a staple cartridge assembly, and a surgical buttress assembly;

FIG. 4 is a perspective view of the staple cartridge assembly of FIG. 3, showing a hook assembly with parts separated;

FIG. 5 is a close-up view of the area of detail 5 indicated in FIG. 3, showing a proximal end portion of the staple cartridge assembly;

FIG. 6 is a top view of the surgical buttress assembly of FIG. 3;

FIG. 7 is a cross-sectional view of the tool assembly of FIG. 2, taken along section line 7-7 of FIG. 2, shown with first and second jaw members of the tool assembly in an open position;

DETAILED DESCRIPTION

Figure 1:
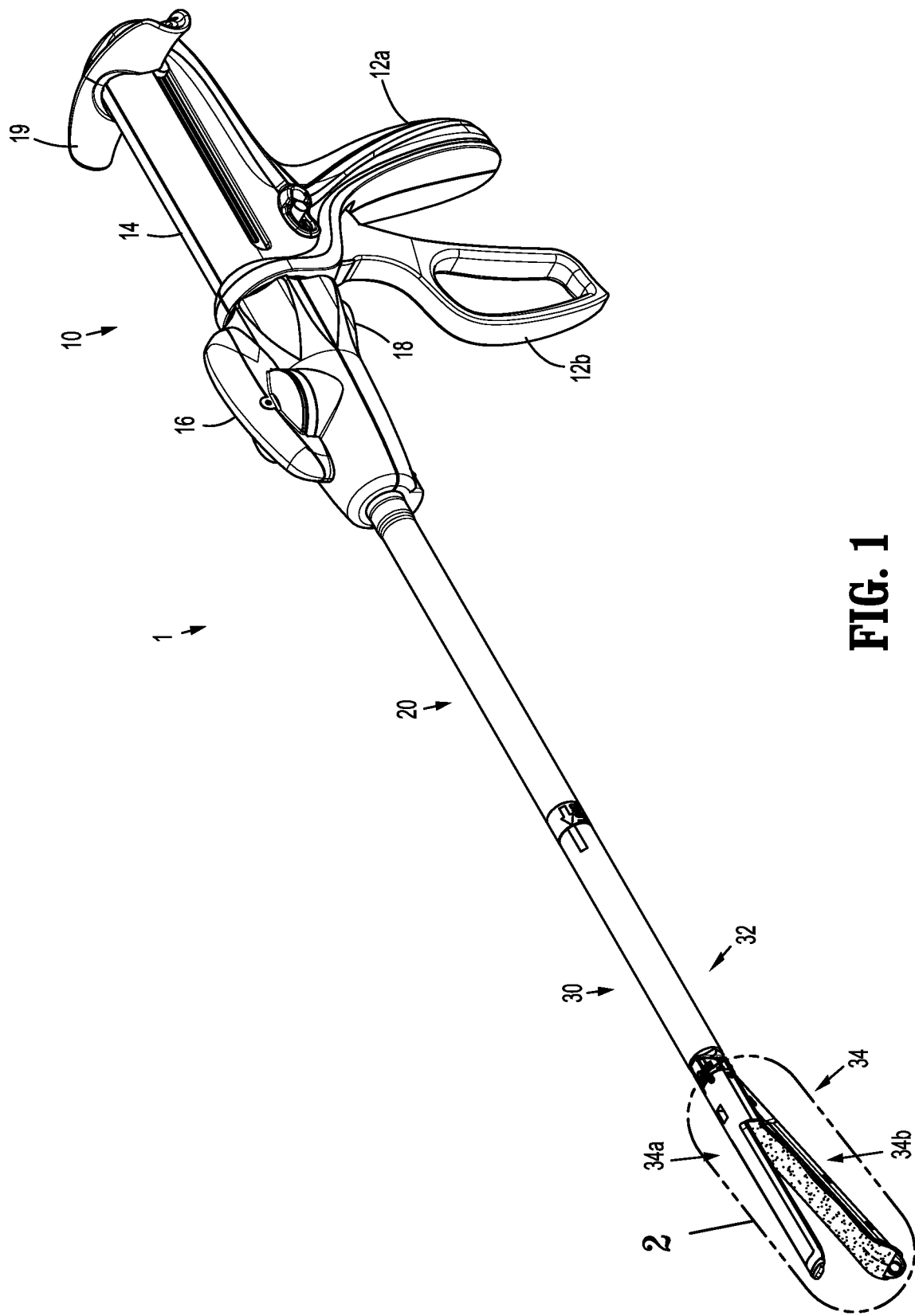
FIG. 1 is a perspective view of a surgical stapling apparatus in accordance with an aspect of the present disclosure.

Aspects of the present disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user.

Referring now to FIG. 1, an exemplary surgical stapling apparatus or surgical stapler 1 is shown for use in stapling tissue in accordance with aspects of the present disclosure. The surgical stapling apparatus 1 will further be described to the extent necessary to disclose aspects of the disclosure. For a detailed description of the structure and function of exemplary surgical stapling apparatus, reference may be made to U.S. Pat. Nos. 6,241,139, 6,330,965, and 7,819,896, the entire contents of each of which are incorporated herein by reference. It should be appreciated that principles of the present disclosure are equally applicable to surgical stapling apparatus having other configurations such as, for example, the types described in U.S. Pat. Nos. 5,964,394, 7,128,253, and 7,334,717, the entire contents of each of which are incorporated herein by reference. Accordingly, it should be understood that a variety of surgical stapling apparatus may be utilized with aspects of the present disclosure. For example, laparoscopic or open staplers, such as, for example, GIA™, Endo GIA™, TA™, and Endo TA™ staplers and/or linear and radial reloads with, for example, Tri-Staple™ technology, available through Medtronic (North Haven, CT) may be utilized with aspects of the present disclosure.

The surgical stapling apparatus 1 generally includes a handle assembly 10, an elongate tubular body 20 extending distally from the handle assembly 10, and a loading unit 30 extending distally from the elongate tubular body 20. The loading unit 30 includes a housing portion 32 and a tool or jaw assembly 34 including first and second jaw members 34a, 34b. The first jaw member 34a and/or the second jaw members 34b is pivotable with respect to the housing portion 32 such that the tool assembly 34 is movable between an open position in which the first and second jaw members 34a, 34b are spaced apart with respect to each other, and a closed position in which the first and second jaw members 34a, 34b are substantially adjacent each other.

The handle assembly 10 includes a stationary handle member 12a, a movable handle member 12b, and a barrel portion 14. Actuation of the movable handle member 12b applies lines of staples to tissue captured between the first and second jaw members 34a, 34b of the tool assembly 34. An articulation lever 16 is mounted on the forward end of the barrel portion 14 to facilitate articulation of the tool assembly 34. A rotatable member 18 is also mounted on the forward end of the barrel portion 14, adjacent the articulation lever 16. Rotation of the rotatable member 18 relative to the barrel portion 14 rotates the elongate tubular body 20 and the loading unit 30 relative to the handle assembly 10 so as to properly orient the tool assembly 34 relative to tissue to be stapled. A knob 19 is movably positionable along the barrel portion 14. The knob 19 is advanced distally to approximate or close the first and second jaw members 34a, 34b of the tool assembly 34 relative to each other, and retracted proximally to unapproximate or open the first and second jaw members 34a, 34b of the tool assembly 34 with respect to each other.

Figure 2:
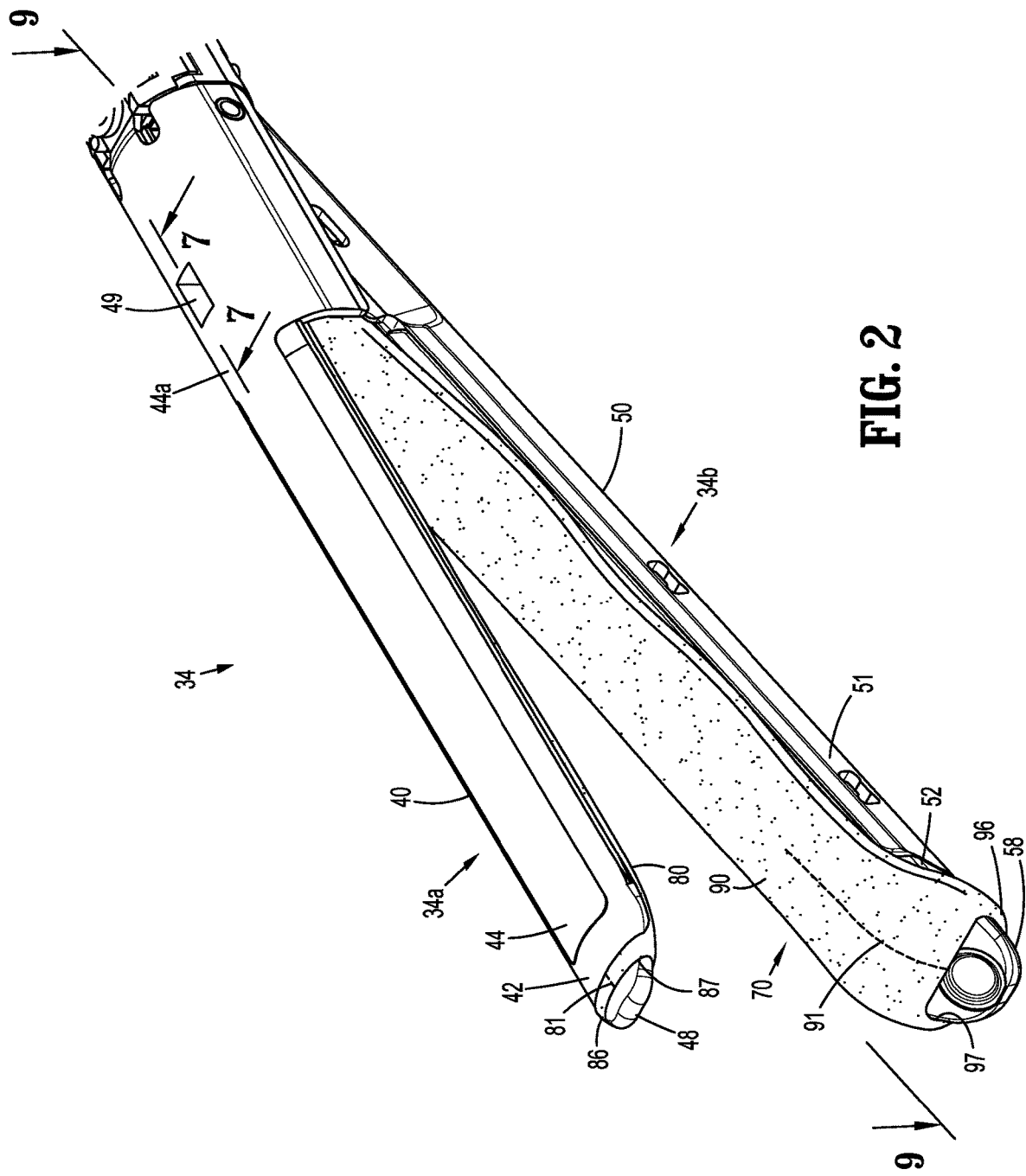
FIG. 2 is a close-up view of the area of detail 2 indicated in FIG. 1, showing a tool assembly of the surgical stapling apparatus.

The loading unit 30 is a disposable loading unit ("DLU") that is releasably secured to the elongated tubular body 20 and thus, replaceable with a new loading unit 30. The loading unit 30 may be a single use loading unit ("SULU") that is used one time and then replaced to facilitate multiples uses of the surgical stapling apparatus 1 on a patient. For example, during a surgical procedure, the surgical stapling apparatus 1 can be used to staple and cut tissue, and the entire SULU is replaced after each staple and cut operation of the surgical stapling apparatus 1. The loading unit 30 may be a multi-use loading unit ("MULU") that is re-useable a predetermined number of times. For example, during a surgical procedure, the surgical stapling apparatus 1 can be used to staple and cut tissue, and a reload assembly (e.g., a staple cartridge 52 as seen in FIG. 2) of the MULU is replaced after each staple and cut operation of the surgical stapling apparatus 1 a pre-determined number of times before the entire MULU needs to be replaced. Alternatively, the loading unit 30 may be permanently affixed to the elongated tubular body 20.

As shown in FIGS. 2 and 3, the first jaw member 34a of the tool assembly 34 includes an anvil assembly 40 and the second jaw member 34b of the tool assembly 34 includes a staple cartridge assembly 50. A surgical buttress 70 is releasably secured to the anvil and staple cartridge assemblies 40, 50.

The anvil assembly 40 includes an anvil plate 42 and a cover plate 44 secured over the anvil plate 42. The anvil plate 42 has a central longitudinal slot 41 formed therein and staple forming pockets or cavities 43 defined in an inward or tissue facing surface thereof 46. An anvil tip 48 extends distal to the staple forming pockets 43, and a window 49 extends through the anvil plate 42 and the cover 44 (e.g., through the tissue facing surface 46 of the anvil plate 42 and an outer surface 44a of the cover 44) proximal to the staple forming pockets 43.

The staple cartridge assembly 50 includes a cartridge carrier 51 and a staple cartridge 52 selectively received and supported within the cartridge carrier 51. The staple cartridge 52 may be removably and/or replaceably attached to the cartridge carrier 51 by, for example, a snap-fit connection, a detent, a latch, among other types of connectors within the purview of those skilled in the art. The staple cartridge 52 includes a cartridge body 54 having an inward or tissue facing surface 56 defining staple pockets or retention slots 55 formed therein. A central longitudinal slot 57 is formed in and extends along a substantial length of the cartridge body 54 to facilitate passage of a knife blade 22 (FIG. 11) of a drive assembly 24 therethrough. A cartridge tip 58 extends distal to the staple pockets 55, and a hook assembly 60 extends outwardly from the tissue facing surface 56 of the cartridge body 54 proximal to the staple pockets 55 and laterally adjacent to the central longitudinal slot 57. The hook assembly 60 is aligned with the window 49 defined in the anvil assembly 40.

As shown in FIGS. 4 and 5, the hook assembly 60 includes a hook 62, a coupler 64, a spring 66, and a retention pin 68. The hook 62 includes a hook body 62a defining an aperture 63 therethrough, and a finger 62b extending proximally from the hook body 62a. The hook body 62a is configured and dimensioned for positioning within a cavity 53 defined in the staple cartridge 52 that is adjacent and open to the central longitudinal slot 57 with the finger 62b extending out of the cavity 53. The retention pin 68 is configured and dimensioned for positioning through a side surface of the staple cartridge 52 and through the aperture 63 of the hook body 62a to pivotally secure the hook 62 to the staple cartridge 52. The coupler 64 and the spring 68 are positionable within the cavity 53 of the staple cartridge 52 for spring-loading the hook 62 into position within the staple cartridge 52. The coupler 64 includes a head 64a, a shaft 64b extending proximally from the head 64a, and a flange 64c disposed between the head 64a and the shaft 64b. A first end portion 66a of the spring 66 is configured for positioning around the shaft 64b of the coupler 64 adjacent and proximal to the flange 64c, and a second end portion 66b of the spring 66 is configured for positioning around a post 53a (FIG. 7) extending distally into the cavity 53 of the staple cartridge 52. The spring 66 biases the head 64a of the coupler 64 into contact with the hook body 62a such that the finger 62b of the hook 62 extends proximally out of the cavity 53 and is disposed above the tissue facing surface 56 of the staple cartridge 52 proximal to the staple pockets 55, as seen in FIG. 5.

With reference now to FIG. 6, the surgical buttress assembly 70 includes an anvil buttress 80 and a cartridge buttress 90 that are formed or joined together as a single continuous structure. The surgical buttress assembly 70 is bent or folded about a central portion thereof (e.g., where the anvil and cartridge buttresses 80, 90 meet), as seen in FIG. 3, such that the anvil and cartridge buttresses 80, 90 substantially overlie one another when loaded on the anvil and staple cartridge assemblies 40, 50. While the anvil and cartridge buttresses 80, 90 are substantially the same (e.g., mirror images of each other), it should be understood that the anvil and cartridge buttresses 80, 90 may be different depending upon the construction of the anvil and staple cartridge assemblies 40, 50.

With continued reference to FIG. 6, in conjunction with FIG. 3, the anvil buttress 80 includes a body 82 configured and dimensioned for positioning on the tissue facing surface 46 of the anvil assembly 40 and covering the staple forming pockets 43, and the cartridge buttress 90 includes a body 92 configured and dimensioned for positioning on the tissue facing surface 56 of the staple cartridge assembly 50 and covering the staple pockets 55. The bodies 82, 92 have a substantially uniform or constant width along the length thereof. The anvil and cartridge buttresses 80, 90 each include a proximal tab 84, 94 extending proximally from the body 82, 92. The proximal tabs 84, 94 are smaller in width than the bodies 82, 92 and, in some aspects, taper proximally from proximal ends of the bodies 82, 92.

The proximal tabs 84, 94 each define a proximal opening 85, 95 therethrough. The proximal openings 85, 95 are configured and dimensioned to extend over the cavity 53 (FIG. 5) defined in the staple cartridge 52 that houses the hook assembly 60 as well as the central longitudinal slots 41, 57 (FIG. 3) of the anvil and staple cartridge assemblies 40, 50. The proximal openings 85, 95 may extend distally into the bodies 82, 92 of the anvil and cartridge buttresses 80, 90. For example, as seen in FIG. 6, the proximal openings 85, 95 have a substantially tear-drop shape including a first or proximal portion 85a, 95a defined in the proximal tab 84, 94 and a second or distal portion 85b, 95b defined in the body 82, 92. The first portion 85a, 95a has a larger dimension than the second portion 85b, 95b such that the first portion 85a, 95a extends over the cavity 53 and the central longitudinal slots 41, 57, as described above, and the second portion 85b, 95b tapers towards and aligns with the central longitudinal slots 41, 57. It should be understood that the proximal openings 85, 95 may have other configurations so long as the proximal openings 85, 95 can engage the finger 62*b* (FIG. 5) of the hook assembly 60 and extend across the central longitudinal slots 41, 57.

The anvil and cartridge buttresses 80, 90 each include a distal tab 86, 96 extending distally from the body 82, 92. The distal tabs 86, 96 have curved ends 86*a*, 96*a* and define a distal opening 87, 97 therethrough. The distal openings 87, 97 are configured and dimensioned to loop around the anvil and cartridge tips 48, 58 (FIG. 3). As seen in FIG. 6, the distal openings 87, 97 have a substantially semi-circular shape that is complementary to the shape of the anvil and cartridge tips 48, 58. It should be understood that the distal openings 87, 97 may have other configurations so long as the distal openings 87, 97 are configured to receive and retain the anvil and cartridge tips 48, 58 therein (e.g., by frictional engagement). The distal tabs 86, 96 further include perforations 81, 91 defined therein that are aligned with the central longitudinal slots 41, 57 (FIG. 3) of the anvil and staple cartridge assemblies 40, 50. The perforations 81, 91 may extend proximally into the bodies 82, 92 of the anvil and cartridge buttresses 80, 90 so that they partially overlie the central longitudinal slots 41, 57.

The surgical buttress assembly 70 is fabricated from biocompatible materials which are bioabsorbable or non-absorbable, natural or synthetic materials. It should be understood that any combination of natural, synthetic, bio-absorbable, and/or non-bioabsorbable materials may be used to form the surgical buttress assembly 70. The anvil buttress 80 and the cartridge buttress 90, or portions thereof, may be formed from the same material or different materials. In aspects, the surgical buttress assembly 70 is formed from a single sheet of material that is cut to shape.

The anvil and cartridge buttresses 80, 90 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The anvil and cartridge buttresses 80, 90 described herein may be a single porous or non-porous layer, or include a plurality of layers including any combination of porous and non-porous layers. For example, the anvil buttress 80 and/or the cartridge buttress 90 may include multiple porous and non-porous layers that are stacked in an alternating manner. In another example, the anvil buttress 80 and/or the cartridge buttress 90 may be formed in a "sandwich-like" manner wherein the outer layers are porous and the inner layer(s) are non-porous, or vice versa. The anvil and cartridge buttresses 80, 90 may have the same or a different structure of layer(s).

Porous layer(s) in a surgical buttress may enhance the ability of the surgical buttress to absorb fluid, reduce bleeding, and/or seal a wound. Also, the porous layer(s) may allow for tissue ingrowth to fix the surgical buttress in place. Non-porous layer(s) in a surgical buttress may enhance the ability of the surgical buttress to resist tears and perforations during the manufacturing, shipping, handling, and/or stapling processes. Also, non-porous layer(s) may retard or prevent tissue ingrowth from surrounding tissues thereby acting as an adhesion barrier and preventing the formation of unwanted scar tissue.

Figure 8:
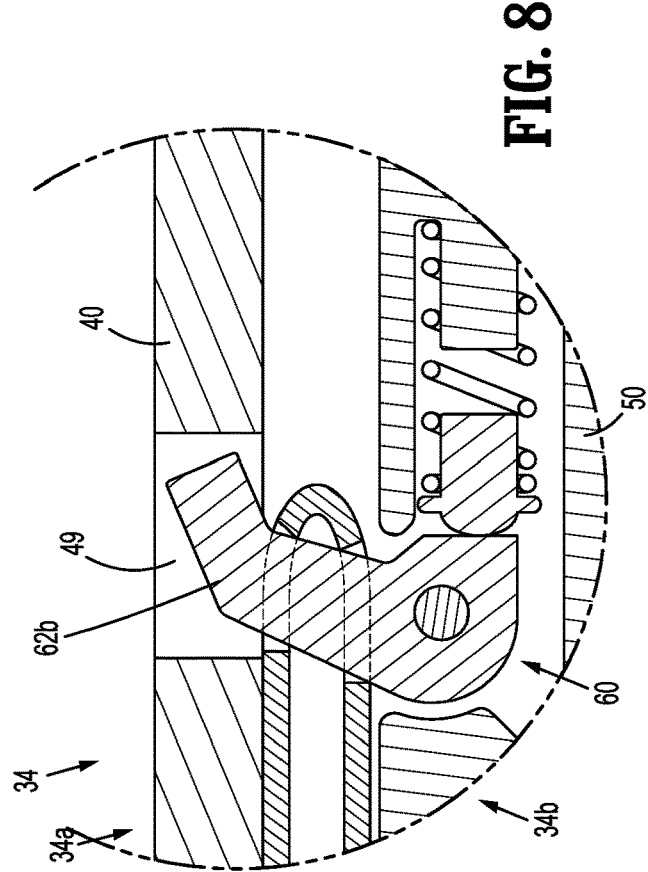
FIG. 8 is a cross-sectional view of the tool assembly of FIG. 7, shown with the first and second jaw members in a closed position.

In a method of loading the surgical buttress assembly 70 onto the loading unit 30, the surgical buttress assembly 70 is folded or bent at the junction between the anvil and cartridge buttresses 80, 90, as seen in FIG. 3, such that the proximal openings 85, 95 are aligned with one another. With the first and second jaw members 34*a*, 34*b* in the open position, as shown in FIG. 7, the surgical buttress assembly 70 is slid between the anvil and staple cartridge assemblies 40, 50 until the proximal tabs 84, 94 are disposed adjacent to the finger 62*b* of the hook assembly 60. The proximal tabs 84, 94 are slid over the finger 62*b* such that the finger 62*b* passes through the proximal openings 85, 95 to retain the proximal tabs 84, 94 of the anvil and cartridge buttresses 80, 90 thereon. The bodies 82, 92 of the anvil and cartridge buttresses 80, 90 are then positioned adjacent to the respective tissue facing surface 46, 56 of the anvil and staple cartridge assemblies 40, 50, and the distal tabs 86, 96 (FIG. 2) of the anvil and cartridge buttresses 80, 90 are engaged with the anvil and cartridge tips 48, 58 via the distal openings 87, 97 to retain the distal tabs 86, 96 of the anvil and cartridge buttresses 80, 90 thereon. Alternatively, the distal tabs 86, 96 may be first secured to the anvil and cartridge tips 48, 58 and then the proximal tabs 84, 94 may then be secured to the finger 62*b* of the hook assembly 60. When the first and second jaw members 34*a*, 34*b* are moved to the closed position, as shown in FIG. 8, the finger 62*b* of the hook assembly 60 extends into the window 49 of the anvil assembly 40 and does not interfere with operation of the tool assembly 34.

The single piece construction of the surgical buttress assembly 70 simplifies the loading process onto a loading unit 30 by reducing the assembly steps required to attach the anvil and cartridge buttresses 80, 90 to the anvil and staple cartridge assemblies 40, 50, and requires only a single fixture (e.g., the hook assembly 60) for securing both the proximal tabs 84, 94 of the anvil and cartridge buttresses 80, 90 to the loading unit 30 at the same time. The surgical buttress assembly 70 may be applied to the loading unit 30 directly without a dedicated applicator or loading tool thereby further simplifying the loading process and saving cost and time.

Figure 9:
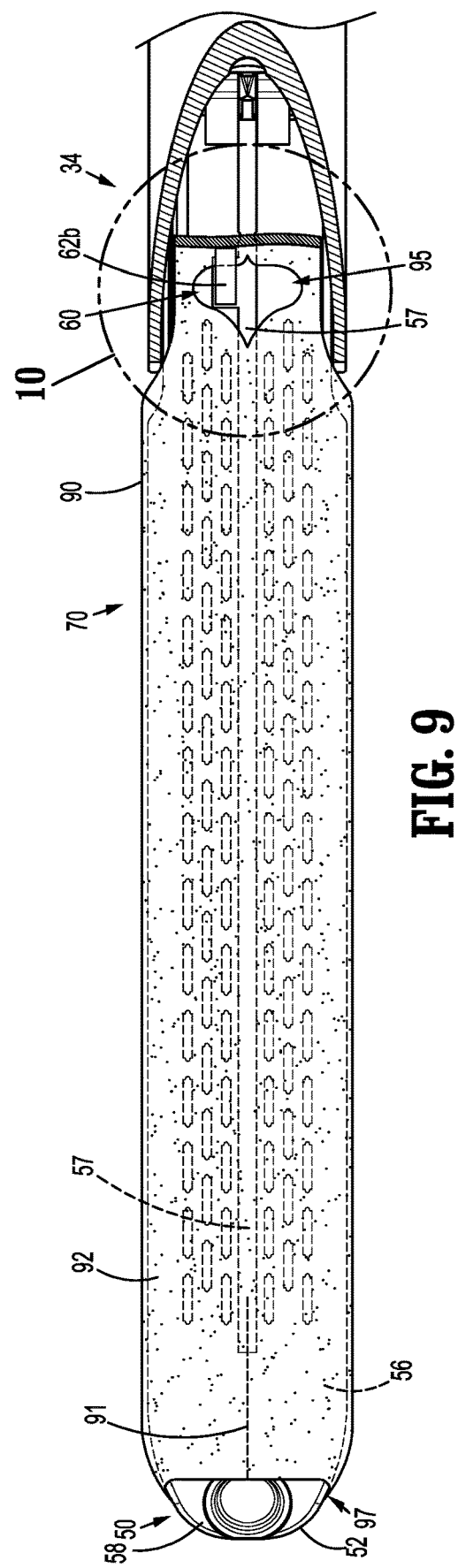
FIG. 9 is a partial cross-sectional view of the tool assembly of FIG. 2, taken along section line 9-9 of FIG. 2.
Figure 10:
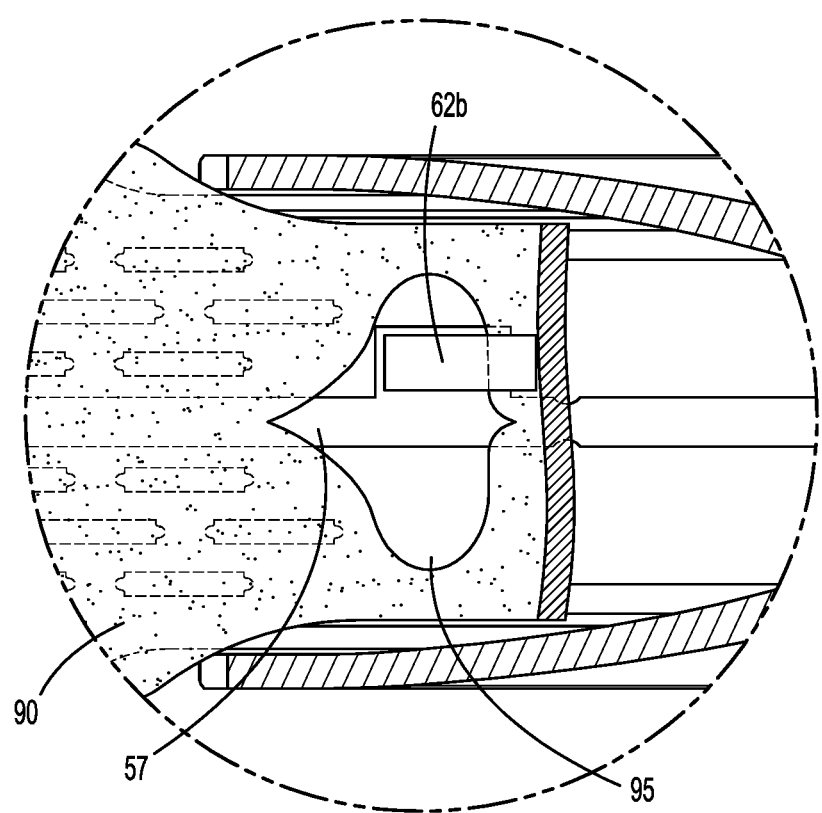
FIG. 10 is a close-up view of the area of detail 10 indicated in FIG. 9.

As shown in FIGS. 9 and 10, when the surgical buttress assembly 70 is loaded on the tool assembly 34, the proximal opening 95 of the cartridge buttress 90 engages the finger 62*b* of the hook assembly 60 and extend across the central longitudinal slot 57 of the staple cartridge assembly 50 and the distal opening 97 engages the cartridge tip 58 such that the body 92 of the cartridge buttress 90 extends across the tissue facing surface 56 of the staple cartridge 52. Additionally, the perforations 91 in the cartridge buttress 90 are aligned with and disposed partially over the central longitudinal slot 57. While only the cartridge buttress 90 and staple cartridge assembly 50 is illustrated in FIGS. 9 and 10, it should be understood that the relationship between the anvil buttress 80 and the anvil assembly 40 is substantially the same as that of the cartridge buttress 90 to the staple cartridge assembly 50 (e.g., the proximal opening 85 of the anvil buttress 80 engages the finger 62*b* of the hook assembly 60, the distal opening 97 engages the anvil tip 48, and the perforations 81 are aligned with the central longitudinal slot 41).

Figure 11:
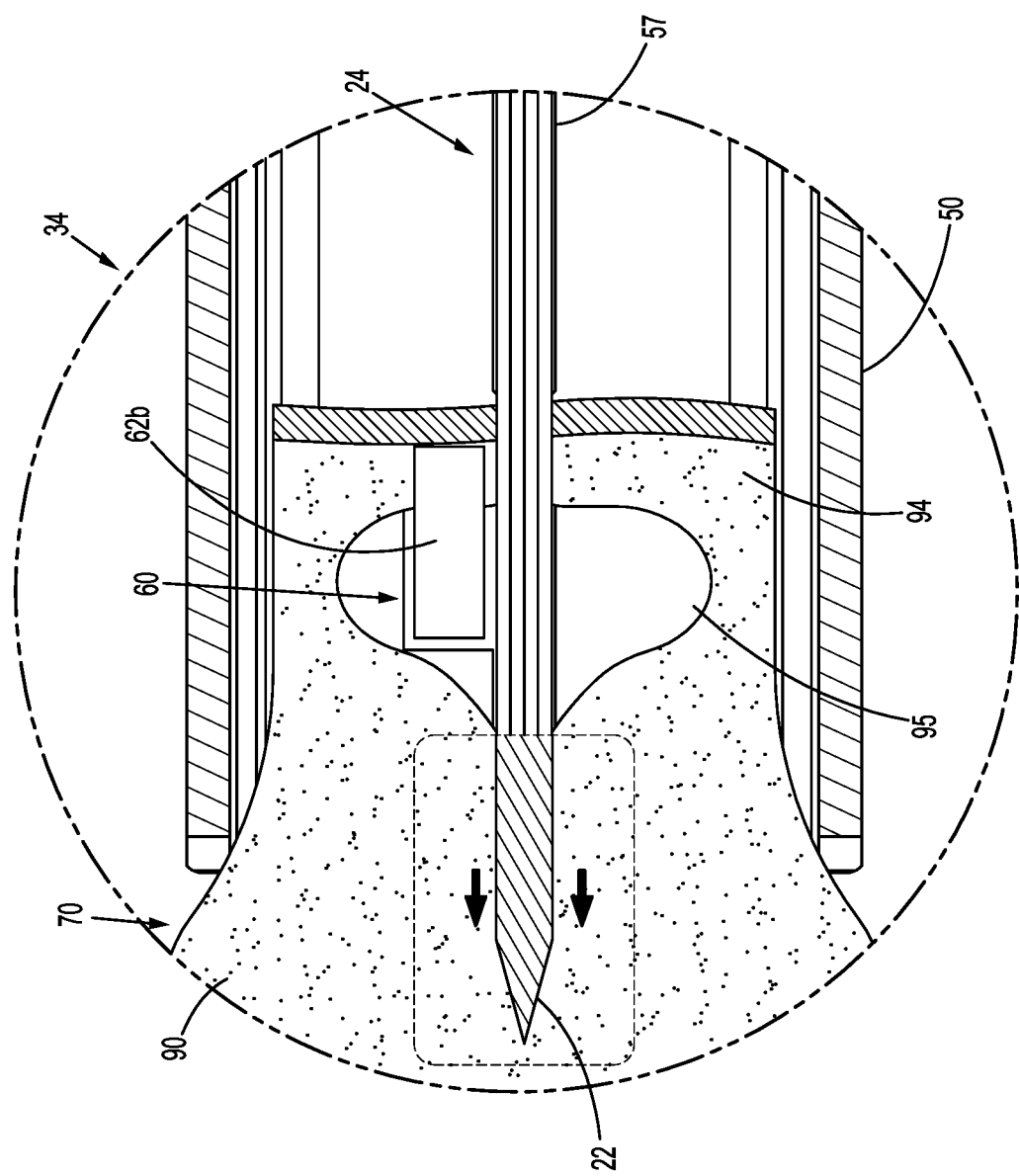
FIG. 11 is a close-up view of the area of detail of FIG. 10, shown during a firing stroke of the surgical stapling apparatus.

The surgical stapling apparatus 1 (FIG. 1), with the loading unit 30 loaded with the surgical buttress assembly 70, is ready for use. In operation, the surgical stapling apparatus 1 is used in accordance with methods known by those skilled in the art. Once the anvil and staple cartridge assemblies 40, 50 are clamped onto tissue, the surgical stapling apparatus 1 is fired, thereby stapling the surgical buttress assembly 70 to the tissue. As shown in FIG. 11, in conjunction with FIG. 3, during firing, the knife blade 22 of the drive assembly 24 travels distally through the central longitudinal slots 41, 57 of the anvil and staple cartridge assemblies 40, 50 and substantially simultaneously cuts and divides the tissue and the surgical buttress assembly 70 disposed between the rows of formed staples. Specifically, the knife blade 22 travels through the proximal tabs 84, 94 and the proximal openings 85, 95 defined therein thereby releasing the proximal tabs 84, 94 of the anvil and cartridge buttresses 80, 90 from the finger 62b of the hook assembly 60. When firing is complete and the anvil and staple cartridge assemblies 40, 50 are unclamped, the anvil and cartridge buttresses 80, 90, which are now stapled to the tissue, pulls away from the anvil and staple cartridge assemblies 40, 50, and the tool assembly 34 can be removed from the surgical site. Specifically, the distal tabs 86, 96 of the anvil and cartridge buttresses 80, 90 are freed from the anvil and cartridge tips 48, 58 by tearing of the distal tabs 86, 96 along the perforations 81, 91 as the surgical buttress assembly 70 pulls away from the anvil and staple cartridge assemblies 40, 50. The used staple cartridge 52 may then be removed from the tool assembly 34 and replaced with a new staple cartridge 52. A new surgical buttress assembly 70 may be installed onto the loading unit 40, as needed or desired, as described above.

Figure 12:
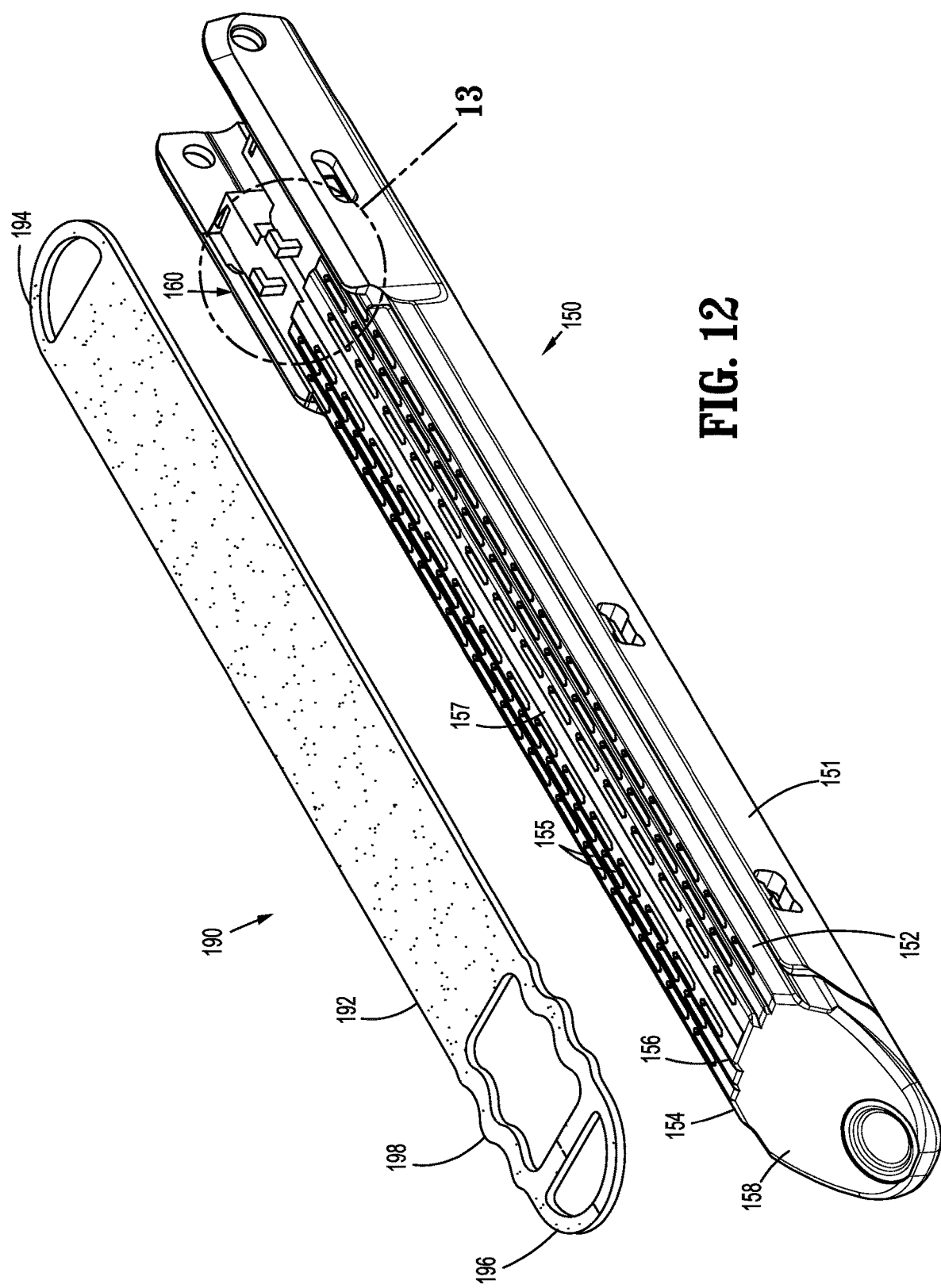
FIG. 12 is a perspective view of a staple cartridge assembly and a cartridge buttress in accordance with another aspect of the present disclosure.

Turning now to FIG. 12, a staple cartridge assembly 150 and a cartridge buttress 190 in accordance with another aspect of the present disclosure suitable for use in a loading unit 30 (FIG. 1) of the surgical stapling apparatus 1 is shown. The staple cartridge assembly 150 is substantially similar to the staple cartridge assembly 50 of FIG. 3. The staple cartridge assembly 150 includes a cartridge carrier 151 and a staple cartridge 152 selectively received and supported within the cartridge carrier 151. The staple cartridge 152 includes a cartridge body 154 having an inward or tissue facing surface 156 defining staple pockets or retention slots 155 formed therein. A central longitudinal slot 157 is formed in and extends along a substantial length of the cartridge body 154 to facilitate passage of a knife blade (not shown) therethrough. A cartridge tip 158 extends from the cartridge body 154 distal to the staple pockets 155, and a hook assembly 160 extends outwardly from the tissue facing surface 156 of the cartridge body 154 proximal to the staple pockets 155.

Figure 13:
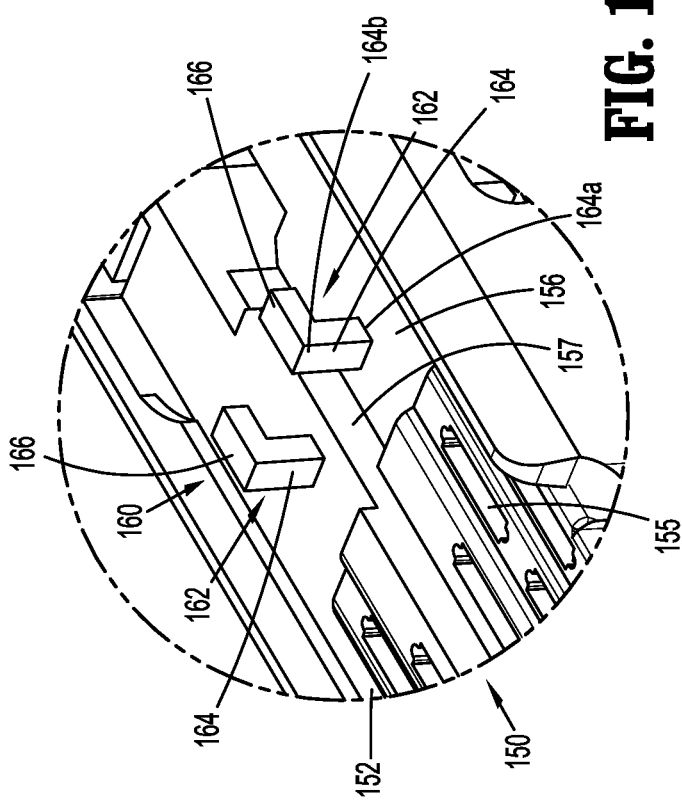
FIG. 13 is a close-up view of the area of detail 13 indicated in FIG. 12, showing a hook assembly of the staple cartridge assembly.

As shown in FIG. 13, the hook assembly 160 includes a pair of hooks 162, with each hook 162 disposed on an opposed side of the central longitudinal slot 157 of the staple cartridge 152. Each hook 162 includes an arm 164 having a first end 164a anchored or secured to the tissue facing surface 156 of the staple cartridge 152 and a second end 164b including a finger 166 extending therefrom. The arm 164 extends upwardly away from the tissue facing surface 156 and the finger 166 extends proximally from the arm 164 such that the finger 166 is disposed in spaced relation relative to the tissue facing surface 156 of the staple cartridge 152. It should be understood that the finger 166 may have other configurations (e.g., be angled, curved, or bent relative to the arm 164, so long as the finger 166 faces proximally for capturing a proximal tab 194 (FIG. 12) of the cartridge buttress 190 thereto, as described in further detail below.

Figure 14:
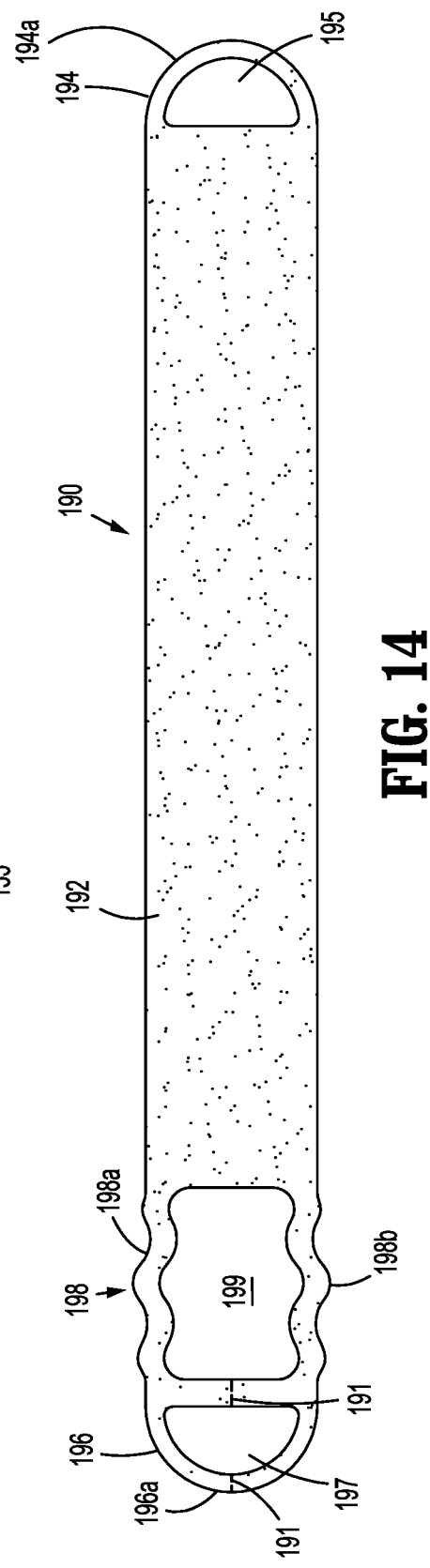
FIG. 14 is a top view of the cartridge buttress of FIG. 12.
Figure 15:
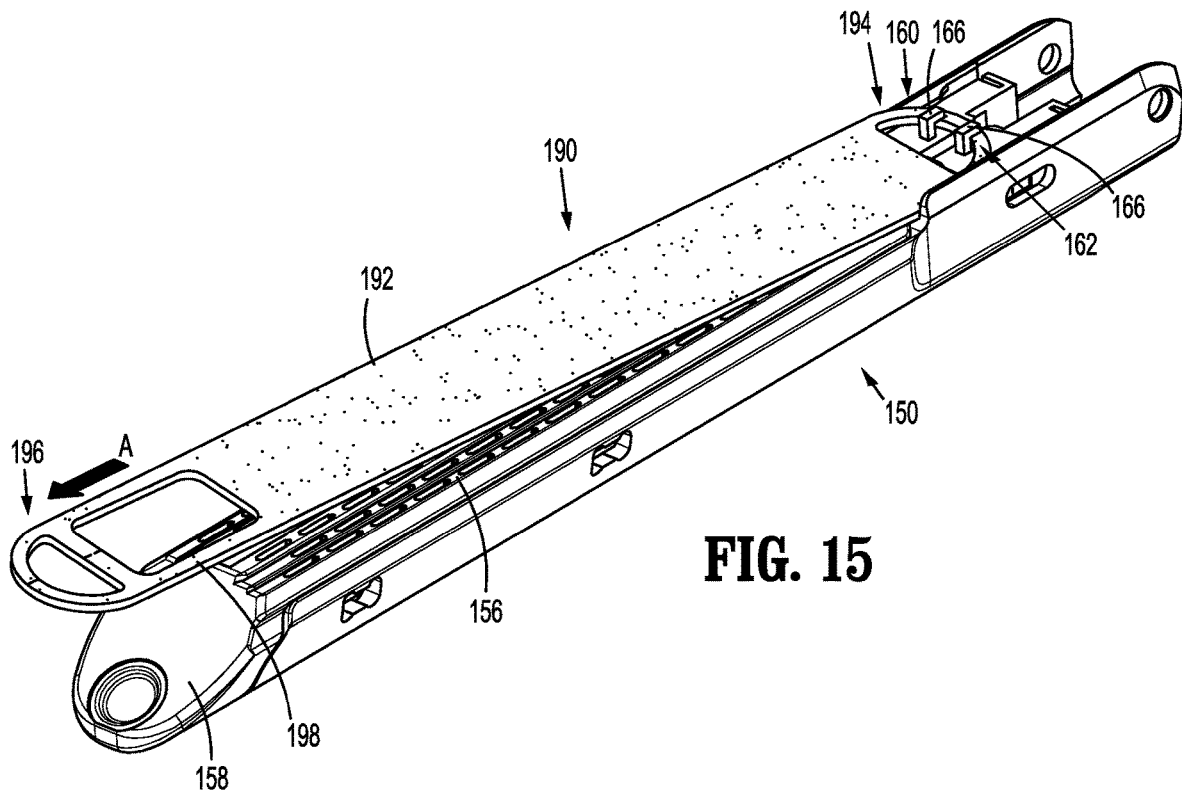
FIG. 15 is a perspective view of the staple cartridge assembly and the cartridge buttress of FIG. 12, shown during assembly of the cartridge buttress onto the staple cartridge assembly with the cartridge buttress in a stretched configuration.

As shown in FIG. 14, the cartridge buttress 190 includes a body 192 configured and dimensioned for positioning on the tissue facing surface 156 (FIG. 13) of the staple cartridge assembly 150 and covering the staple pockets 155. A proximal tab 194 extends proximally from the body 192. The proximal tab 194 defines a proximal opening 195 therethrough and has a curved proximal end 194a. The proximal opening 195 is configured and dimensioned to engage the hook assembly 160 (FIG. 13) of the staple cartridge 152. The cartridge buttress 190 includes an expandable region 198 extending distally from the body 192 and a distal tab 196 extending distally from the expandable region 198. The expandable region 198 is configured to transition between a biased or unexpanded state (FIG. 14) to an expanded state (FIG. 15) upon application of a force thereto to temporarily elongate the cartridge buttress 190 axially from an original or unstretched configuration (FIG. 14) to a stretched configuration (FIG. 15). While the expandable region 198 is shown as a pair of elastic bands 198a, 198b interconnecting the body 192 and the distal tab 196, and having an opening 199 defined therebetween, it should be understood that other configurations of the expandable region 198 are envisioned (e.g., the expandable region 198 may be a solid piece of material). The distal tab 196 defines a distal opening 197 therethrough and has a curved distal end 196a. The distal opening 197 is configured and dimensioned to engage the cartridge tip 158 (FIG. 12) of the staple cartridge assembly 150. The distal tab 196 further includes perforations 191 defined therein that are aligned with the central longitudinal slot 157 (FIG. 12) of the staple cartridge assembly 150.

The cartridge buttress 190 is fabricated from biocompatible materials which are bioabsorbable or non-absorbable, natural or synthetic materials, as described above with regard to the surgical buttress assembly 70 of FIG. 6. The body 192, the proximal tab 194, and the distal tab 196 of the cartridge buttress 190 may be formed from the same or different materials that are relatively rigid as compared to the material(s) forming the expandable region 198. Accordingly, while the body 192, the proximal tab 194, and the distal tab 196 of the cartridge buttress 190 may be flexible and have a little give (e.g., when formed from fibers and/or a foam), stretching of the cartridge buttress 190 primarily occurs in the expandable region 198. The expandable region 198 is formed from elastic materials that stretch upon application of a force thereto and return to its original shape in the absence of the force.

Figure 16:
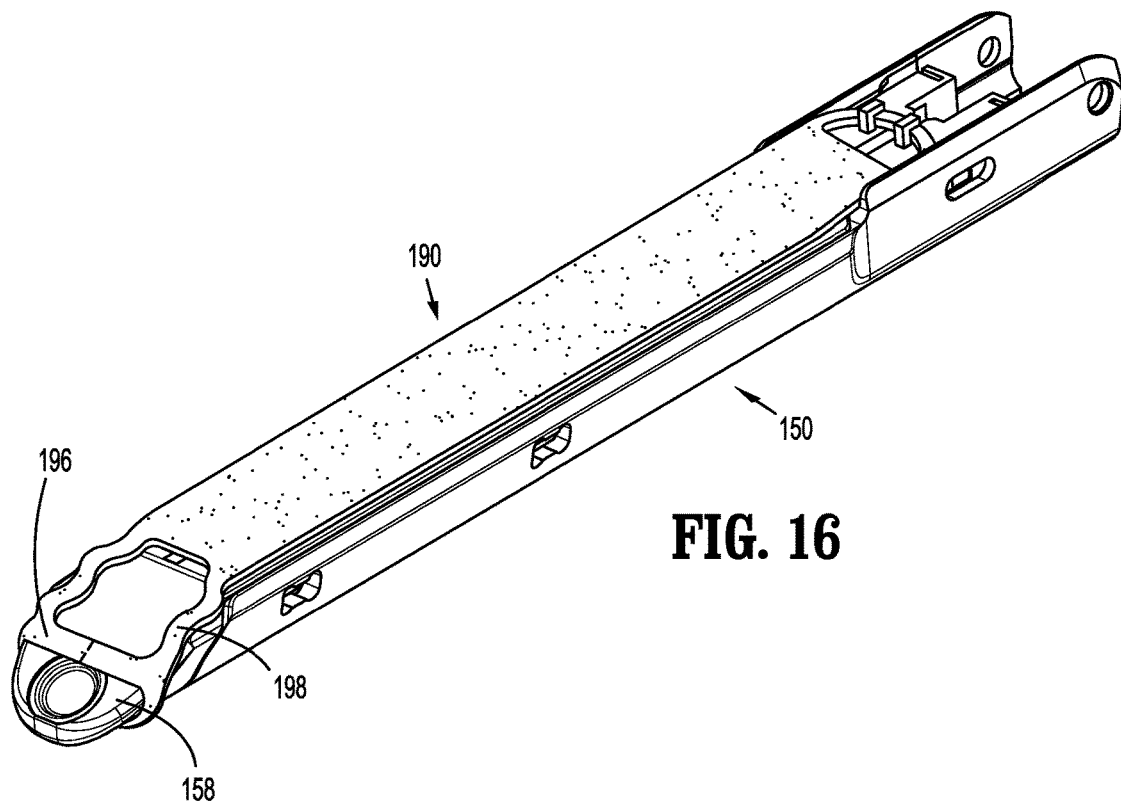
FIG. 16 is a perspective view of the staple cartridge assembly and the cartridge buttress of FIG. 15, shown with the cartridge buttress loaded onto the staple cartridge assembly with the cartridge buttress in an unstretched configuration.

In a method of loading the cartridge buttress 190 onto the staple cartridge assembly 150, the proximal tab 194 of the cartridge buttress 190 is slid over the hooks 162 of the hook assembly 160 such that the fingers 166 pass through the proximal opening 195 to retain the proximal tab 194 of the cartridge buttress 190 thereon, as shown in FIG. 15. The distal tab 196 of the cartridge buttress 190 is then pulled distally in the direction of arrow "A" such that the body 192 of the cartridge buttress 190 extends over the tissue facing surface 156 of the staple cartridge assembly 150 and the expandable region 198 transitions to the expanded state so that the distal tab 196 can be looped around the cartridge tip 158. Upon engagement of the distal tab 196 with the cartridge tip 158, as seen in FIG. 16, the expandable region 198 returns to its unexpanded state and the staple cartridge assembly 150, loaded with the cartridge buttress 190, is ready for use.

Figure 17:
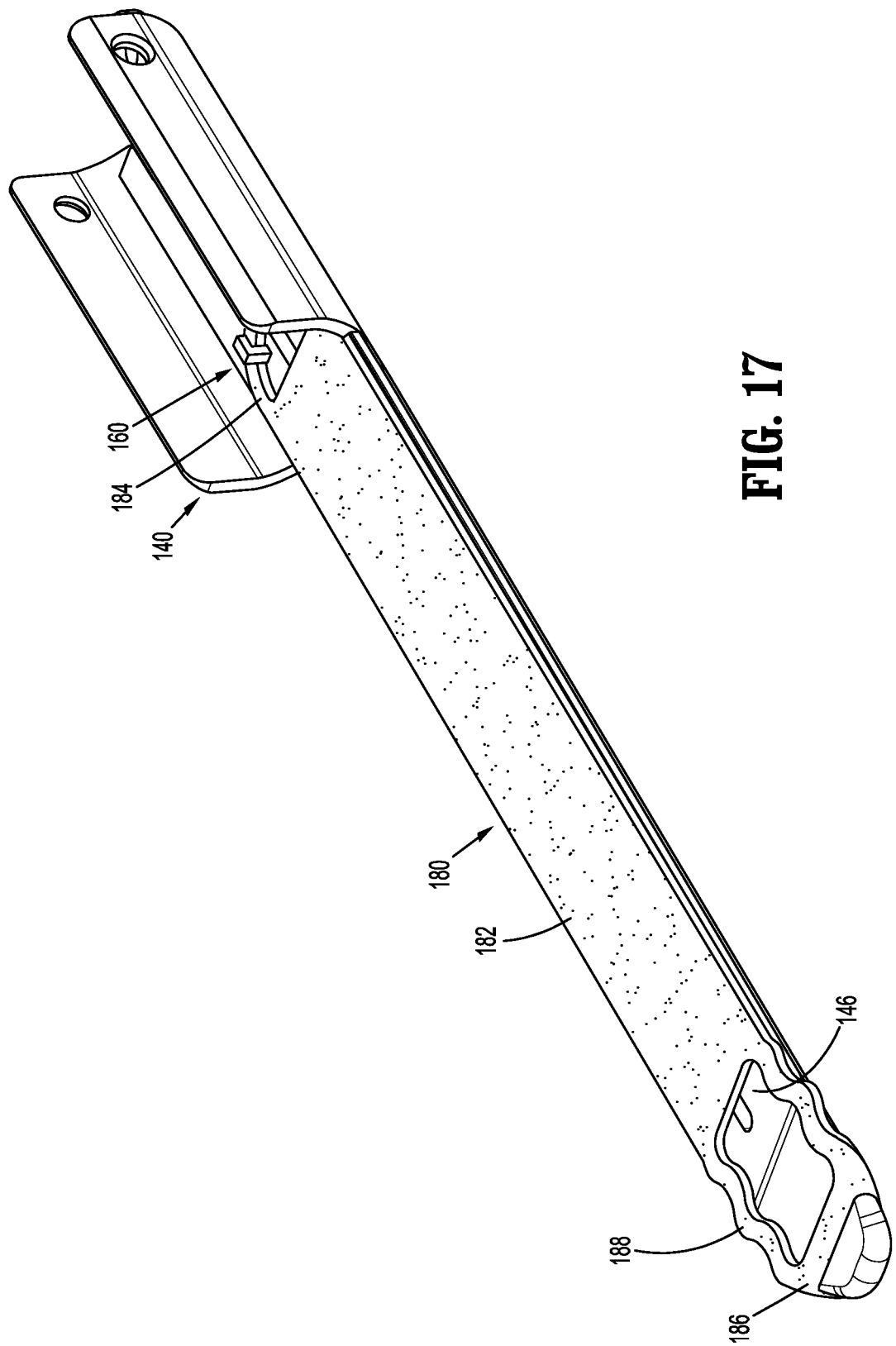
FIG. 17 is a perspective view of an anvil assembly and an anvil buttress loaded onto the anvil assembly in accordance with another aspect of the present disclosure.

Additionally or alternatively, as shown in FIG. 17, an anvil assembly 140 may include a hook assembly 160 for releasably securing a proximal tab 184 of an anvil buttress 180 to the anvil assembly 140. The anvil buttress 180 is substantially the same as the cartridge buttress 190 and includes a body 182 configured and dimensioned for positioning on the tissue facing surface 146 of the anvil assembly 140, a proximal tab 184 extending proximally from the body 182, an expandable region 188 extending distally from the body 182, and a distal tab 186 extends distally from the expandable region 188. In aspects in which both the staple cartridge assembly 150 and the anvil assembly 140 include a hook assembly 160, the hook assemblies 160 are positioned in either lateral or longitudinal spaced relation relative to each other so as not to interfere with open and closing of the first and second jaw members 34a, 34b (FIG. 1).

The expandable region 188, 198 of the anvil and cartridge buttresses 180, 190 minimizes the occurrence of buttress deformation during the loading process by returning the anvil and cartridge buttresses 180, 190 back to their original shape (e.g., providing tension or tautness) after the anvil and cartridge buttresses 180, 190 have been elongated during assembly over the hook assembly 160 and/or the anvil or cartridge tips 148, 158. The anvil and cartridge buttresses 180, 190 may be applied to the loading unit 30 directly without a dedicated applicator or loading tool thereby simplifying the loading process and saving cost and time.

While illustrated as being used on a hand-held manually actuated surgical device hereinabove, it is contemplated, and within the scope of the present disclosure for the loading unit 30 to be configured for use with various electromechanical surgical instruments and/or electrosurgical instruments. For example, the loading unit 30 may be configured to be detachably coupleable and controllable by a handheld electromechanical surgical device, such as the handheld electromechanical surgical system shown and described in U.S. Patent Appl. Pub. No. 2016/0310134, the entire content of which is incorporated herein by reference. As another example, the loading unit 30 may be configured to detachably coupleable and controllable by a robotic surgical system, such as the robotic surgical system shown and described in U.S. Patent Appl. Pub. No. 2012/0116416, the entire content of which is incorporated herein by reference.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Additionally, the elements and features shown and described in connection with certain aspects of the disclosure may be combined with the elements and features of certain other aspects without departing from the scope of the present disclosure, and that such modifications and variation are also included within the scope of the present disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. A surgical stapling apparatus comprising:
   a loading unit including an anvil assembly and a staple cartridge assembly, the staple cartridge assembly including:
   a staple cartridge having a cartridge body and a cartridge tip extending distally from the cartridge body, the cartridge body including a tissue facing surface having staple pockets and a central longitudinal slot defined therethrough; and
   a hook assembly extending outwardly from the tissue facing surface; and
   a cartridge buttress including a body, a proximal tab extending proximally from the body, an expandable region extending distally from the body, and a distal tab extending distally from the expandable region, the proximal tab engaged with the hook assembly of the staple cartridge for releasably securing the proximal tab of the cartridge buttress to the staple cartridge assembly and the distal tab engaged with the cartridge tip for releasably securing the distal tab of the cartridge buttress to the staple cartridge assembly.

2. The surgical stapling apparatus according to claim 1, wherein the expandable region of the cartridge buttress is transitionable between an unexpanded state and an expanded state to elongate the cartridge buttress during loading onto the staple cartridge assembly.

3. The surgical stapling apparatus according to claim 1, wherein the expandable region of the cartridge buttress is formed from an elastic material.

4. The surgical stapling apparatus according to claim 3, wherein the body and the proximal and distal tabs of the cartridge buttress are formed from a relatively rigid material as compared to the elastic material of the expandable region.

5. The surgical stapling apparatus according to claim 1, wherein the expandable region of the cartridge buttress includes a pair of bands interconnecting the body and the distal tab.

6. The surgical stapling apparatus according to claim 5, wherein the pair of bands of the expandable region of the cartridge buttress defines an opening therebetween.

7. The surgical stapling apparatus according to claim 6, wherein the opening of the expandable region is positioned over the staple cartridge at a location distal to the staple pockets.

8. The surgical stapling apparatus according to claim 1, wherein the proximal tab of the cartridge buttress defines a proximal opening therethrough and the hook assembly extends through the proximal opening.

9. The surgical stapling apparatus according to claim 8, wherein the proximal opening of the proximal tab extends across the central longitudinal slot defined in the staple cartridge.

10. The surgical stapling apparatus according to claim 1, wherein the distal tab of the cartridge buttress defines a distal opening therethrough and the cartridge tip extends through the distal opening.

11. The surgical stapling apparatus according to claim 1, wherein the hook assembly includes hooks disposed on opposed sides of the central longitudinal slot of the staple cartridge.

12. The surgical stapling apparatus according to claim 11, wherein each of the hooks includes an arm secured to the tissue facing surface of the staple cartridge and a finger extending proximally from the arm.

13. The surgical stapling apparatus according to claim 1, wherein the distal tab of the cartridge buttress includes perforations aligned with the central longitudinal slot of the staple cartridge.

14. A surgical stapling apparatus comprising:
   a loading unit including:
   an anvil assembly including an anvil plate having a tissue facing surface and an anvil tip extending distally from the anvil plate;
   a staple cartridge assembly including a staple cartridge having a cartridge body and a cartridge tip extending distally from the cartridge body, the cartridge body having a tissue facing surface; and
   a hook assembly extending outwardly from the tissue facing surface of the anvil plate or the cartridge body; and
   a surgical buttress including a body, a proximal tab extending proximally from the body, an expandable region extending distally from the body, and a distal tab extending distally from the expandable region, the proximal tab engaged with the hook assembly for releasably securing the proximal tab to the anvil assembly or the staple cartridge assembly and the distal tab engaged with the anvil tip or the cartridge tip for releasably securing the distal tab to the anvil assembly or the staple cartridge assembly.

15. The surgical stapling apparatus according to claim 14, wherein the expandable region of the surgical buttress is transitionable between an unexpanded state and an expanded state to elongate the surgical buttress during loading onto the loading unit.

16. The surgical stapling apparatus according to claim 14, wherein the expandable region of the surgical buttress is formed from an elastic material.

17. The surgical stapling apparatus according to claim 14, wherein the expandable region of the surgical buttress includes a pair of bands interconnecting the body and the distal tab, the pair of bands defining an opening therebetween.

18. The surgical stapling apparatus according to claim 14, wherein the proximal tab of the surgical buttress defines a proximal opening therethrough, and the hook assembly extends through the proximal opening.

19. The surgical stapling apparatus according to claim 14, wherein the distal tab of the surgical buttress defines a distal opening therethrough, and the anvil tip or the cartridge tip extends through the distal opening.

20. The surgical stapling apparatus according to claim 14, wherein the hook assembly includes hooks disposed on opposed sides of a central longitudinal slot defined through the tissue facing surface of the anvil plate or the cartridge body.

* * * * *